US012676217B2

(12) United States Patent
Austring

(10) Patent No.: US 12,676,217 B2
(45) Date of Patent: Jul. 7, 2026

(54) SYSTEM AND METHOD OF PROPERTY COLLECTION MANAGEMENT AND ARCHITECTURE

(71) Applicant: Synerio Technologies, Inc., Fort Worth, TX (US)

(72) Inventor: Ronald Raymond Austring, English Harbour (AG)

(73) Assignee: Technologies IP, LLC., Fort Worth, TX (US)

( * ) Notice: Subject to any disclaimer, the term of this patent is extended or adjusted under 35 U.S.C. 154(b) by 665 days.

(21) Appl. No.: 17/730,923

(22) Filed: Apr. 27, 2022

(65) Prior Publication Data

US 2022/0254462 A1 Aug. 11, 2022

Related U.S. Application Data

(63) Continuation-in-part of application No. 17/105,097, filed on Nov. 25, 2020, now abandoned.

(60) Provisional application No. 63/201,383, filed on Apr. 27, 2021, provisional application No. 63/201,385, filed on Apr. 27, 2021, provisional application No. 63/201,387, filed on Apr. 27, 2021, provisional application No. 63/201,386, filed on Apr. 27, 2021, (Continued)

(51) Int. Cl.
G16H 10/60 (2018.01)

(52) U.S. Cl.
CPC .................................. G16H 10/60 (2018.01)

(58) Field of Classification Search
CPC ............................... G16H 10/60; G16H 15/00
See application file for complete search history.

(56) References Cited

U.S. PATENT DOCUMENTS

| | | | | |
|---|---|---|---|---|
| 5,832,450 A | * | 11/1998 | Myers .................... | G16H 10/60 705/3 |
| 6,163,801 A | * | 12/2000 | O'Donnell .............. | G06F 9/544 709/215 |
| 10,296,297 B2 | | 5/2019 | Kumar et al. | |

(Continued)

OTHER PUBLICATIONS

PCT International Application No. PCT/US2022/026538, International Search Report and Written Opinion dated Aug. 23, 2022; 9 pages.

(Continued)

*Primary Examiner* — Merilyn P Nguyen
(74) *Attorney, Agent, or Firm* — Whitaker Chalk Swindle & Schwartz PLLC; Juan Vasquez; Enrique Sanchez, Jr.

(57) ABSTRACT

A system and method of property collection management and architecture that can organize patient data while maintaining context is presented. The present disclosure provides for a database system implementing a 'Property Collection' as a collection of 'property name' and 'property value' pairs, which are used to describe a 'data entity.' Further, the present disclosure can provide for historical access to data to track data changes. The present disclosure solves the technological problem of accessing data having differing data for the same person. The immutable electronic health record data storage system solves the aforementioned technological problem by providing a blockchain, transaction blockchain API, serialization module, and a deserialization module, among others that can format, process, and store data in a Global Patient Record (GPR).

20 Claims, 7 Drawing Sheets

Related U.S. Application Data provisional application No. 63/201,388, filed on Apr. 27, 2021.

(56)                    References Cited

U.S. PATENT DOCUMENTS

| | | | | |
|---|---|---|---|---|
| 10,850,604 | B2 * | 12/2020 | Pieper | F16D 13/52 |
| 10,860,622 | B1 * | 12/2020 | Florissi | G06F 16/22 |
| 11,036,703 | B1 | 6/2021 | Shaughnessy | |
| 11,475,053 | B1 * | 10/2022 | Das | G06F 16/3344 |
| 2002/0059299 | A1 | 5/2002 | Spaey | |
| 2003/0101169 | A1 | 5/2003 | Bhatt et al. | |
| 2005/0192649 | A1 * | 9/2005 | Shehadeh | A61N 1/37211 |
| | | | | 607/60 |
| 2007/0061393 | A1 * | 3/2007 | Moore | H04L 67/02 |
| | | | | 709/201 |
| 2008/0270181 | A1 * | 10/2008 | Rosenberg | G16H 10/20 |
| | | | | 705/7.42 |
| 2008/0319942 | A1 * | 12/2008 | Courdy | G06Q 10/10 |
| 2010/0094910 | A1 * | 4/2010 | Bayliss | G06Q 10/10 |
| | | | | 707/E17.096 |
| 2010/0281020 | A1 * | 11/2010 | Drubner | G06F 16/245 |
| | | | | 707/769 |
| 2012/0215560 | A1 * | 8/2012 | Ofek | G16H 70/20 |
| | | | | 705/3 |
| 2013/0013342 | A1 | 1/2013 | Morris | |
| 2014/0136237 | A1 * | 5/2014 | Anderson | G16H 10/60 |
| | | | | 705/3 |
| 2014/0379615 | A1 | 12/2014 | Brigham et al. | |
| 2016/0004820 | A1 | 1/2016 | Moore | |
| 2016/0070758 | A1 * | 3/2016 | Thomson | G16H 10/60 |
| | | | | 707/781 |
| 2016/0077901 | A1 | 3/2016 | Roth et al. | |
| 2016/0292456 | A1 * | 10/2016 | Dubey | G06F 16/21 |
| 2017/0161435 | A1 | 6/2017 | Orosco | |
| 2017/0212783 | A1 * | 7/2017 | Choi | G06F 9/5061 |
| 2017/0235969 | A1 | 8/2017 | Kamara et al. | |
| 2018/0285337 | A1 | 10/2018 | Wagh et al. | |
| 2019/0354693 | A1 | 11/2019 | Yoon et al. | |
| 2020/0012676 | A1 | 1/2020 | Narang et al. | |
| 2020/0305802 | A1 * | 10/2020 | Archambault | A61B 5/0002 |
| 2020/0320061 | A1 | 10/2020 | Korpman et al. | |
| 2021/0090694 | A1 | 3/2021 | Colley et al. | |
| 2021/0117436 | A1 | 4/2021 | Zabel et al. | |
| 2021/0209145 | A1 * | 7/2021 | Oliner | G06F 16/43 |
| 2022/0011866 | A1 * | 1/2022 | Kim | G06F 3/16 |
| 2022/0092566 | A1 * | 3/2022 | Austring | G06Q 10/10 |
| 2022/0254462 | A1 * | 8/2022 | Austring | G16H 10/60 |

OTHER PUBLICATIONS

PCT International Appl. No. PCT/US22/26593 International Search Report and Written Opinion, 7 pages, mailed Aug. 26, 2022.

* cited by examiner

500

502

Receive array of 'Property Collection' references

504

Iterate through the received array until the
'Address-Property Collection' is identified

506

Retrieve array of 'Property Collection' references using
the 'Get Property Value As Array Of Property
Collections' function on the 'Property Collection' object

SYSTEM AND METHOD OF PROPERTY COLLECTION MANAGEMENT AND ARCHITECTURE

CROSS-REFERENCE TO RELATED APPLICATIONS

The present application is a Continuation-in-Part of U.S. patent application Ser. No. 17/105,097, filed Nov. 25, 2020, entitled "SYSTEM AND METHOD FOR DATA PRO-VIDER TRACKING AND MONETIZATION," which claims priority to U.S. Provisional Patent Application Ser. No. 63/080,412, filed Sep. 18, 2020, entitled "DATA PRO-VIDER TRACKING AND MONETIZATION SYSTEM," and U.S. Provisional Patent Application Ser. No. 63/110,807, filed Nov. 6, 2020, entitled "PATIENT DATA PROVI-SION, CONSUMPTION, AND ROYALTY PROCESSING SYSTEM," and further claims priority to U.S. Provisional Patent Application Ser. No. 63/201,383, filed on Apr. 27, 2021, entitled "ADDRESSABLE UNIVERSAL DATA LOCATOR SYSTEM FOR PROGRAM EXECUTION AND METHOD THEREFOR," U.S. Provisional Patent Application Ser. No. 63/201,385, filed on Apr. 27, 2021, entitled "ELECTRONIC HEALTH RECORD PERMIS-SIONING SYSTEM AND METHOD," U.S. Provisional Patent Application Ser. No. 63/201,388, filed on Apr. 27, 2021, entitled "ELECTRONIC HEALTH RECORD DATA QUALIFICATION SYSTEM AND METHOD," U.S. Pro-visional Patent Application Ser. No. 63/201,387, filed on Apr. 27, 2021, entitled "SERVER PROTOCOL FORMAT-TING SYSTEM AND METHOD," and U.S. Provisional Patent Application Ser. No. 63/201,386, filed on Apr. 27, 2021, entitled "PROPERTY COLLATION SYSTEM AND METHOD," the contents of which are incorporated herein in their entireties for all purposes.

TECHNICAL FIELD

The present disclosure generally relates to data storage and structuring, and more specifically to a collection of 'property name' and 'property value' pairs, which can be used to describe a 'data entity'.

BACKGROUND

Numerous healthcare providers participate in each phase of care. Healthcare service providers, including pharmacies, physicians, hospitals, laboratories, clinics, medical institu-tions, and regulatory agencies that develop clinical standards of care, historically have operated their own data systems, typically according to unique and different formats and processes.

A patient's private information, including the patient's name, address, phone number, social security number, insur-ance information, medical history, clinical information, and other relevant information, can be stored in an Electronic Health Record (EHR) database, such as an Electronic Patient Outcome Record (EPOR), Solid POD, XML, file, or other suitable data storage element.

Often times a "complete" picture of a patient is not realizable due to different "holes" in a patient's EPO data. These holes exist because typically, each generator of patient data specializes in only its particular area and has no means to consume and provided data from other generator of patient data for a particular patient. No data structure has been proffered to handle all of the disparate data generated by various data generators for a patient. Even more difficult would be to incorporate non-healthcare data in an attempt to generate a "complete" picture of a person that extends beyond a patient. Further, there has been no incentive for patient data generators to share their data with others. The sharing of data has an inherent cost associated with the maintenance and transfer of that data. With tightening bud-gets and diminishing support, even in-person requests for medical records can take months to acquire.

SUMMARY

The present disclosure achieves technical advantages as a system and method of property collection management and architecture that can organize patient data while maintaining context. The present disclosure provides for a system inte-grated into a practical application with meaningful limita-tions directed toward database systems involving a 'Property Collection' as a collection of 'property name' and 'property value' pairs, which are used to describe a 'data entity.' Further, the present disclosure can provide for historical access to data to track data changes. A property value can contain a: 'String,' 'Integer,' 'Decimal,' 'Date,' 'Time,' 'DateTime,' 'Boolean,' 'Byte Array,' a 'Property Collection Reference' (e.g., a reference to another Property Collection), or an array of 'Property Collection References.' When a 'Property Collection' references another 'Property Collec-tion,' in a 'nested' form, it represents entity relationships.

The present disclosure solves the technological problem of accessing data having differing data for the same person. The immutable electronic health record data storage system solves the aforementioned technological problem by pro-viding a blockchain, transaction blockchain API, serializa-tion module, and a deserialization module, among others that can format, process, and store data in a Global Patient Record (GPR). Such modules can be implemented in one or more servers coupled to memory (local, network, distrib-uted, or otherwise). Accordingly, the claims herein are necessarily rooted in computer technology as they overcome a problem arising in the realm of computer database storage, access, and data transmission.

The present disclosure provides a technological solution missing from conventional systems by providing a system that can correct data field errors by consolidating data for a person across disparate data sources. Additionally, the sys-tem can implement an Execution Context Property Path (XPP) that can access a 'property' within a 'Property Col-lection,' a 'property' within a graph of nested 'Property Collections,' or a 'property' within an array of 'Property Collections.' In one embodiment, an XPP can be an ascii string consisting of several components to address a 'prop-erty.' For example, the XPP can be formatted according to the following structure: <property collection><property path><query string>. Moreover, the system can serialize data to facilitate immutable data storage in an efficient manner.

Accordingly, the present disclosure discloses concepts inextricably tied to computer technology such that the present disclosure provides the technological benefit of optimizing database technology to consolidate and correct data, while efficiently storing the data, and addressing prop-erty collection properties with a historical view. The present disclosure technologically surpasses conventional technol-ogy as the present disclosure allows for immutable data storage via an immutable data storage protocol. The con-cepts taught by the present disclosure can be used in any data-centric industry but are particularly relevant in the healthcare industry (e.g., clinical, pharmaceutical, etc.).

It is an object of the invention to provide a system for property collection management and architecture. It is a further object of the invention to provide a method of property collection management and architecture. These and other objects are provided by the present disclosure, including at least the following embodiments.

In another embodiment, a system for property collection management and architecture can include: a global patient record database storing a plurality of property collections; and a computer processor operably coupled to the global patient record database and capable of executing machine-readable instructions to perform program steps, the program steps comprising: generating an empty property collection for a person, the property collection having an execution context property path (XPP); adding a plurality of fields from a request for data that was received from a client to the property collection; identifying empty fields in the property collection; searching other property collections for the person and adding missing data to the property collection for the person; identifying differences in a first field of the other property collections by correlating the ASCII values between the first fields; and conducting a statistical analysis of the values of the field over multiple time entries to identify the correct first field value. Wherein the correlation can include a field of a property collection across multiple timestamps to identify the correct first data field and can overwrite the first data field in the property collection. Wherein the statistical analysis can include an average, mean, or median. The program steps further comprising returning validated data to the client, such that any missing information is provided and any erroneous information is corrected. The program steps further comprising building a history of commands to create a property collection for different times. The program steps further comprising adding a timestamp as metadata to the property collection. The program steps further comprising annotating a provider of missing data. The program steps further comprising annotating a property operation such that an audit trail can be created. The program steps further comprising using timestamps for each property collection, to identify and retrieve information for the person for a particular date. The program steps further comprising repopulating data just prior to an errant data change.

In another embodiment, a method of property collection management and architecture can include: generating an empty property collection for a person, the property collection having an execution context property path (XPP); adding, via a processor, a plurality of fields from a request for data that was received from a client to the property collection; identifying empty fields in the property collection; searching other property collections for the person and adding missing data to the property collection for the person; identifying differences in a first field of the other property collections by correlating the ASCII values between the first fields; and conducting a statistical analysis of the values of the field over multiple time entries to identify the correct first field value. Wherein the correlation can include a field of a property collection across multiple timestamps to identify the correct first data field and can overwrite the first data field in the property collection. Wherein the statistical analysis can include an average, mean, or median. Further comprising returning validated data to the client, such that any missing information is provided and any erroneous information is corrected. Further comprising building a history of commands to create a property collection for different times. Further comprising adding a timestamp as metadata to the property collection. Further comprising annotating a provider of missing data. Further comprising annotating a property operation such that an audit trail can be created. Further comprising using timestamps for each property collection, to identify and retrieve information for the person for a particular date. Further comprising repopulating data just prior to an errant data change.

BRIEF DESCRIPTION OF THE DRAWINGS

The present disclosure will be readily understood by the following detailed description, taken in conjunction with the accompanying drawings that illustrate, by way of example, the principles of the present disclosure. The drawings illustrate the design and utility of one or more exemplary embodiments of the present disclosure, in which like elements are referred to by like reference numbers or symbols. The objects and elements in the drawings are not necessarily drawn to scale, proportion, or precise positional relationship. Instead, emphasis is focused on illustrating the principles of the present disclosure.

DETAILED DESCRIPTION

The disclosure presented in the following written description and the various features and advantageous details thereof, are explained more fully with reference to the non-limiting examples included in the accompanying drawings and as detailed in the description. Descriptions of well-known components have been omitted to not unnecessarily obscure the principal features described herein. The examples used in the following description are intended to facilitate an understanding of the ways in which the disclosure can be implemented and practiced. A person of ordinary skill in the art would read this disclosure to mean that any suitable combination of the functionality or exemplary embodiments below could be combined to achieve the subject matter claimed. The disclosure includes either a representative number of species falling within the scope of the genus or structural features common to the members of the genus so that one of ordinary skill in the art can recognize the members of the genus. Accordingly, these examples should not be construed as limiting the scope of the claims.

A person of ordinary skill in the art would understand that any system claims presented herein encompass all of the elements and limitations disclosed therein, and as such, require that each system claim be viewed as a whole. Any reasonably foreseeable items functionally related to the claims are also relevant. Pursuant to Section 904 of the Manual of Patent Examination Procedure, the Examiner, after having obtained a thorough understanding of the invention disclosed and claimed in the nonprovisional application has searched the prior art as disclosed in patents and other published documents, i.e., nonpatent literature. Therefore, as evidenced by the issuance of this patent, the prior art fails to disclose or teach the elements and limitations presented in the claims as enabled by the specification and drawings, such that the presented claims are patentable under 35 U.S.C. §§ 101, 102, 103, and 112.

Figure 1:
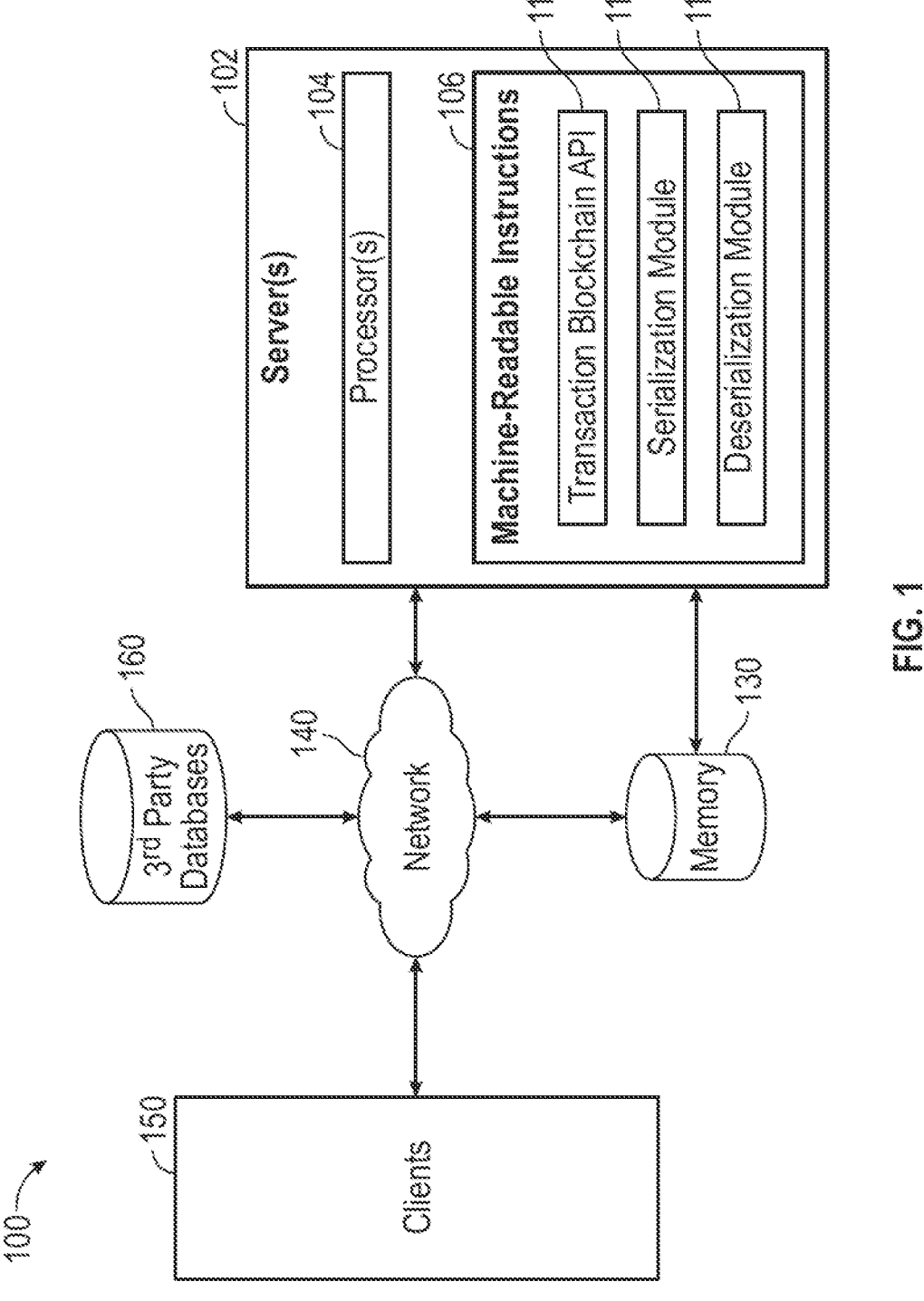
FIG. 1 illustrates a system schematic, in accordance with one or more exemplary embodiments of the present disclosure.

FIG. 1 illustrates a schematic view of a property collection management and architecture system 100, in accordance with one or more exemplary embodiments of the present disclosure. The system 100 can include one or more servers 102 having one or more processors 104, a memory 130, machine readable instructions 106, including transaction blockchain API 110, a serialization module 112, and a deserialization module 114, among other relevant modules. The server 102 can be operably coupled to one or more clients 150 via a network 140. The clients can be a physical device (e.g., mobile phone, laptop, tablet, desktop computer, wearable device, or other suitable device), program, or application. In another exemplary embodiment, a client can include a mobile phone having a mobile application configured to communicate with the server 102 over the network 140.

In one embodiment, a transaction blockchain API 110 can be provided by the system 100 for accessing the blockchain, the transaction blockchain API 110 having an interface that defines interactions between multiple components. For example, the blockchain API 110 can define the kinds of calls or requests that can be made, how to make them, the data formats that should be used, the conventions to follow, and other suitable functionality related to a blockchain. In another embodiment, the blockchain API 110 can access and retrieve Property Collections.

In one embodiment, a serialization module 112 can converting a 'Property Collection' into a 'byte array' such that the contents of the 'Property Collection' can be written to, and read from, for example, a BLOB based storage medium in an efficient manner. Serialization can support an optional 'Property Name Mapping', which allows a property name string to be converted to an integer. This process reduces the size of the 'byte array' significantly.

In one embodiment, a deserialization module 114 can convert a 'byte array' into a 'Property Collection' such that the contents of the 'Property Collection' can be reconstructed from storage in, for example, a BLOB based storage medium in an efficient manner.

The aforementioned systems, components, and modules can be communicably coupled to each other via the network 140, such that data can be transmitted therebetween. The network 140 can be the Internet, intranet, computer bus, or other suitable network. The data transmission can be encrypted, unencrypted, over a VPN tunnel, or other suitable communication means. The network 140 can be a WAN, LAN, PAN, or other suitable network type. The network communication can be encrypted using PGP, Blowfish, Twofish, AES, 3DES, HTTPS, or other suitable encryption. The system 100 can be configured to provide communication via the various systems, components, and modules disclosed herein via an application programming interface (API), PCI, PCI-Express, ANSI-X12, Ethernet, Fiber, Wi-Fi, Bluetooth, or other suitable communication protocol or medium. Additionally, third party systems and databases 160 can be operably coupled to the system components via the network 140.

The data transmitted to and from the components of system 100 (e.g., the server 102, memory 130, and clients 150), can include any format, including the Execution Context Property Path (XPP) format disclosed herein, JavaScript Object Notation (JSON), TCP/IP, XML, HTML, ASCII, SMS, CSV, representational state transfer (REST), or other suitable format. The data transmission can include a message, flag, header, header properties, metadata, and/or a body, or be encapsulated and packetized by any suitable format having same.

The server(s) 102 can be implemented in hardware, software, or a suitable combination of hardware and software therefor, and may comprise one or more software systems operating on one or more servers, having one or more processors 104, with access to memory 130. Server(s) 102 can include electronic storage, one or more processors, and/or other components. Server(s) 102 can include communication lines, connections, and/or ports to enable the exchange of information via a network 140 and/or other computing platforms. Server(s) 102 can also include a plurality of hardware, software, and/or firmware components operating together to provide the functionality attributed herein to server(s) 102. For example, server(s) 102 can be implemented by a cloud of computing platforms operating together as server(s) 102, including Software-as-a-Service (SaaS) and Platform-as-a-Service (PaaS) functionality. Additionally, the server(s) 102 can include memory 130, locally attached, network attached, or both.

Memory 130 can comprise electronic storage that can include non-transitory storage media that electronically stores information. The electronic storage media of electronic storage can include one or both of system storage that can be provided integrally (e.g., substantially non-removable) with server(s) 102 and/or removable storage that can be removably connectable to server(s) 102 via, for example, a port (e.g., a USB port, a firewire port, etc.) or a drive (e.g., a disk drive, etc.). Electronic storage may include one or more of optically readable storage media (e.g., optical disks, etc.), magnetically readable storage media (e.g., magnetic tape, magnetic hard drive, floppy drive, etc.), electrical charge-based storage media (e.g., EEPROM, RAM, etc.), solid-state storage media (e.g., flash drive, etc.), and/or other electronically readable storage media. Electronic storage may include one or more virtual storage resources (e.g., cloud storage, a virtual private network, and/or other virtual storage resources). The electronic storage can include a database, or public or private distributed ledger (e.g., blockchain). In one embodiment, memory 130 can be a blockchain implemented on one or more platforms, including BigChainDB, nChain, Ethereum, Hyperledger, R3, Ripple, EOS, or other suitable blockchain platform. The blockchain can be a public blockchain (accessible to the general public) or a private blockchain (accessible only by those parties credentialed for access). Electronic storage can store machine-readable instructions 106, software algorithms, control logic, data generated by processor(s), data received from server(s), data received from computing platform(s), and/or other data that can enable server(s) to function as described herein. The electronic storage can also include third-party databases accessible via the network 140.

Processor(s) 104 can be configured to provide data processing capabilities in server(s) 102. As such, processor(s) 104 can include one or more of a digital processor, an analog processor, a digital circuit designed to process information, an analog circuit designed to process information, a state machine, and/or other mechanisms for electronically processing information, such as FPGAs or ASICs. The processor(s) 104 can be a single entity or include a plurality of processing units. These processing units can be physically located within the same device, or processor(s) 104 can represent processing functionality of a plurality of devices or software functionality operating alone, or in concert.

The processor(s) 104 can be configured to execute machine-readable instructions 106 or machine learning modules via software, hardware, firmware, some combination of software, hardware, and/or firmware, and/or other mechanisms for configuring processing capabilities on processor(s) 104. As used herein, the term "machine-readable instructions" can refer to any component or set of components that perform the functionality attributed to the machine-readable instructions component 106. This can include one or more physical processors 104 during execution of processor-readable instructions, the processor-readable instructions, circuitry, hardware, storage media, or any other components.

The server(s) 102 can be configured with machine-readable instructions having one or more functional modules. The machine-readable instructions 106 can be implemented on one or more servers 102, having one or more processors 104, with access to memory 130. The machine-readable instructions 106 can be a single networked node, or a machine cluster, which can include a distributed architecture of a plurality of networked nodes. The machine-readable instructions 106 can include control logic for implementing various functionality, as described in more detail below. The machine-readable instructions 106 can include certain functionality associated with the system 100. Additionally, the machine-readable instructions 106 can include a smart contract or multi-signature contract that can process, read, and write data to the memory 130, 3rd party database 160, including a database, distributed ledger, or blockchain.

Figure 2A:
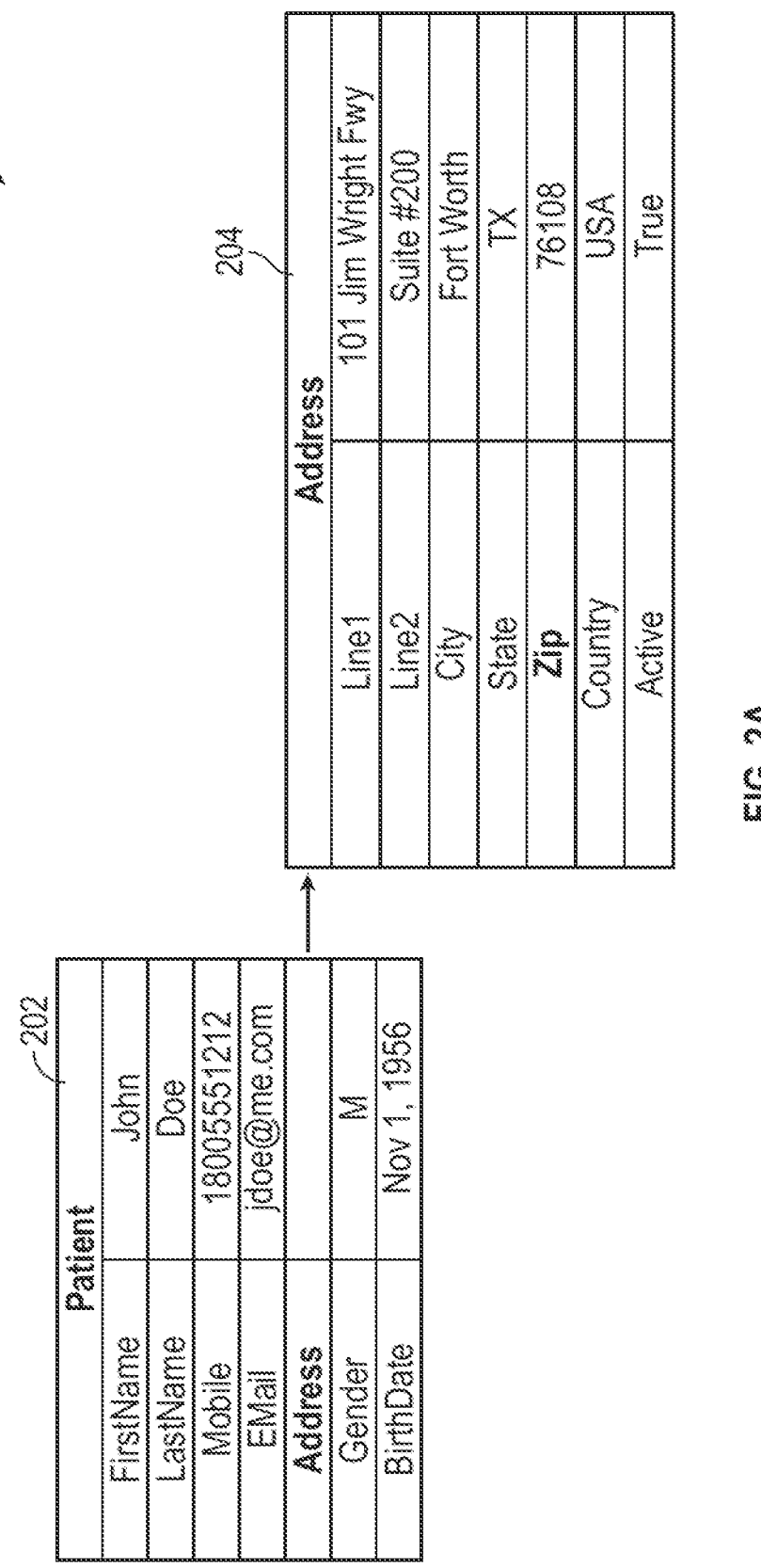
FIGS. 2A and 2B illustrate logical diagrams of portion of a property collection, in accordance with one or more exemplary embodiments of the present disclosure.
Figure 2B:
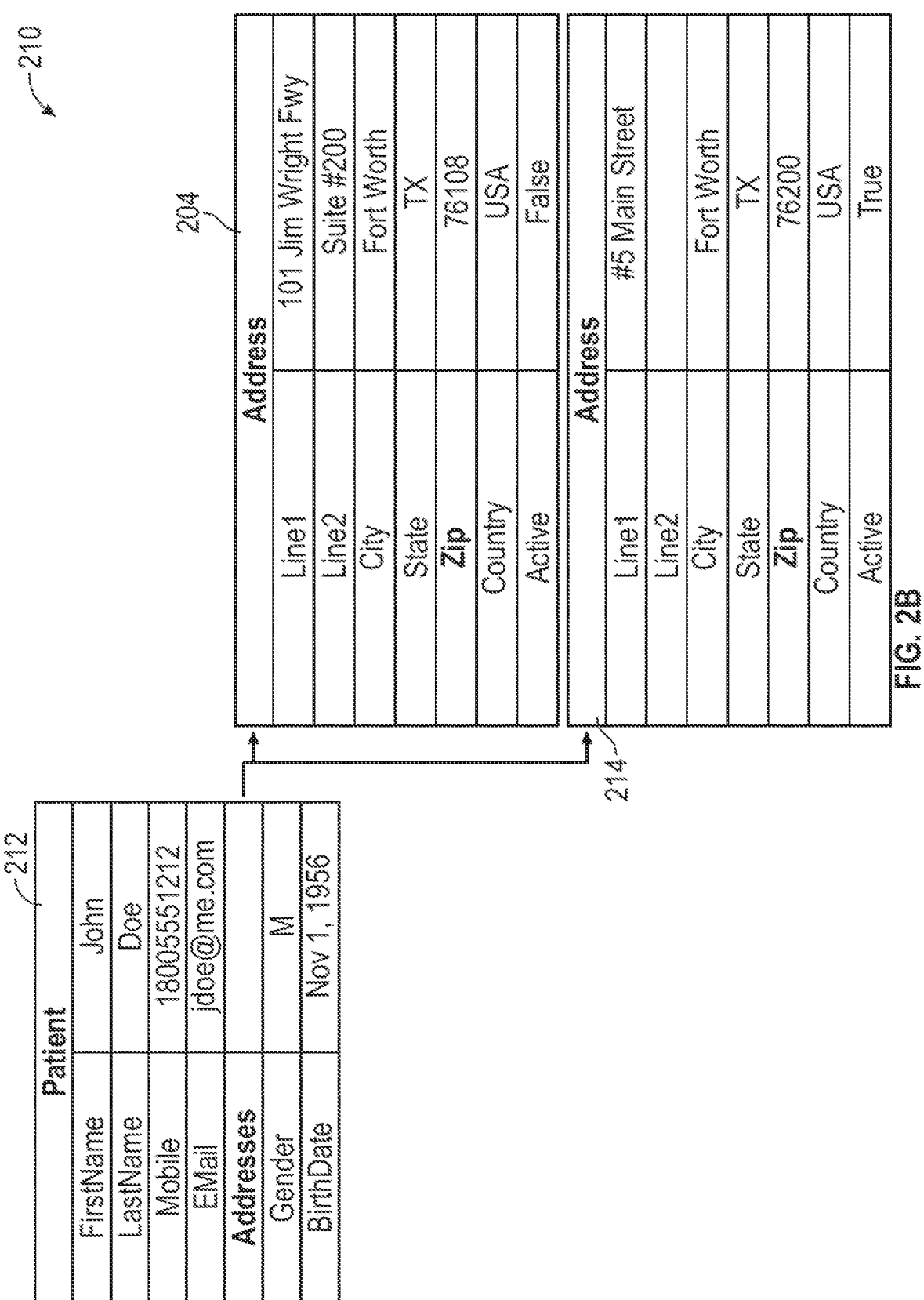

FIGS. 2A and 2B illustrate logical diagrams of portion of data associated with a property collection, referred to generally as 200, in accordance with one or more exemplary embodiments of the present disclosure. FIG. 2A shows a 'property collection' named 'Patient' 202, can have one or more fields and values associated with the Patient property collection 202. For example, the property collection 202 can include fields such as 'First Name, 'Last Name,' 'Mobile,' 'Email,' 'Address,' 'Gender,' and 'Birthdate,' to name a few. The 'Address' field 204 can include multiple fields such as 'Line 1,' 'Line 2,' 'City,' 'State,' Zip,' 'Country,' and 'Active,' to name a few.

FIG. 2B shows a 'property collection' named 'Patient' 212, can have one or more fields and values associated with the Patient property collection 212, however, the 'Address' field 204 can be an array of Property Collections. In one embodiment, a 'Property Value' within a 'Property Collection' can reference an array of 'Property Collection' references. This can be another form of a nested 'Property Collection', but the key difference only becomes apparent when accessing a 'property,' within an array of 'Property Collections,' since an 'index' can be used to select the desired 'Property Collection' within the array. The first 'Property Collection' in an array of 'Property Collection' references can be accessed using an 'index' value of 0. The 'Address' field can be an Address array that can have multiple address entries 204, 214 for a particular patient. For example, the address array entries can include multiple fields such as 'Line 1,' 'Line 2,' 'City,' State,"Zip," Country,' and 'Active,' to name a few. Address array entries may be the same, have missing information in some entries, or be completely different, based on when the address information was populated. In another embodiment, Property Collections can reference other Property Collections in a nested fashion to form an object graph. There is no theoretical limit to the number of levels of reference. If the root 'Property Collection' is serialized, the entire graph of 'Property Collections' can be serialized as well. When the root 'Property Collection' is deserialized the entire graph of 'Property Collections' can be restored.

Figures 3, 4A:
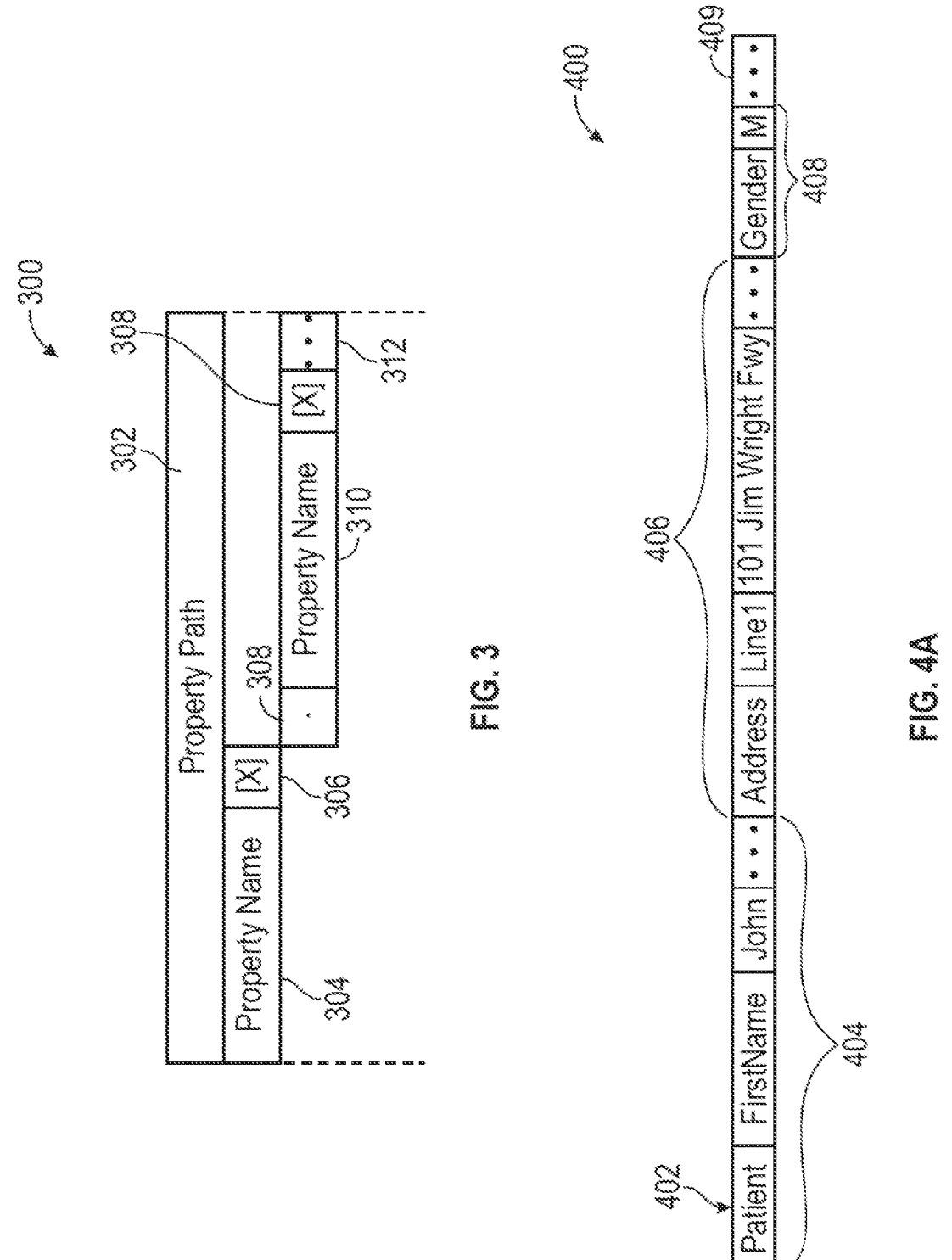
FIG. 3 shows a schematic of a property path 300, in accordance with one or more embodiments of the present disclosure.
FIGS. 4A-4C illustrate diagrams of a serialized byte array, writing byte arrays, and reading byte arrays, respectively, in accordance with one or more embodiments of the present disclosure.

FIG. 3 shows a schematic of a property path 300, in accordance with one or more embodiments of the present disclosure. In one embodiment, to communicate the location of any single piece of data or a collection of data within an application program, a data item, within an application program, can package itself within a 'Property Collection' and register that 'Property Collection' with the 'execution context.' Another benefit of having all data within an application registered, and addressable, is that the current state of an 'execution context' can be saved (e.g., and later restored), simply by setting all the 'Property Collections' to persist their contents to some kind of storage medium (cache, database, flat file, etc.). At some time in the future, to restore the 'execution context', the 'Property Collections' can simply be read back from the storage medium.

An XPP can be similar to a 'property path,' 302 but the first 'name' in the 'property path,' is the name of a 'property collection.' An XPP might only be used in association with an 'execution context.' In general, an XPP is a technology that provides a consistent way to address and access 'Property Collection' data within an 'execution context' of an application. For example, to access the 'Name' property of the 'Patient' property collection, the XPP could be: "Patient.Name." If referencing a 'nested' property collection, the XPP can begin with the name of the 'Property Collection' (e.g., 'Patient'), following by the 'property path' that forms the address of the nested property (e.g., Patient.Address.Zip).

In one embodiment, the 'execution context' can also support 'property access methods' for each data type supported by property collections. As a minimum, these methods accept an XPP as an argument and can be used to read (e.g., get) and write (e.g., put) property values. The execution context can also support a method used to retrieve a 'property value' as an 'object.' This retrieval method can used by the 'qualification engine' when data types are discovered at 'runtime.' Examples of 'put' and 'get' property types are shown below:

Get Property Value

| Property Type | Method Name |
| --- | --- |
| String | getPropertyValueAsString |
| SByte | getPropertyValueAsSInt08 |
| Byte | getPropertyValueAsUInt08 |
| Int16 | getPropertyValueAsSInt16 |
| UInt16 | getPropertyValueAsUInt16 |
| Int32 | getPropertyValueAsSInt32 |
| UInt32 | getPropertyValueAsUInt32 |
| Int64 | getPropertyValueAsInt64 |
| UInt64 | getPropertyValueAsUInt64 |
| Decimal | getPropertyValueAsDecimal |
| Boolean | getPropertyValueAsBoolean |
| UInt32 | getPropertyValueAsDate |
| UInt32 | getPropertyValueAsTime |
| UInt64 | getPropertyValueAsDateTime |
| Byte[ ] | getPropertyValueAsByteArray |
| Object | getPropertyValueAsObject |
| List<ITpePropertyCollection> | getPropertyValueAsArrayOfPropertyCollections |

Put Property Value

| Property Type | Method Name |
|---|---|
| String | putPropertyValueAsString |
| SByte | putPropertyValueAsSInt08 |
| Byte | putPropertyValueAsUInt08 |
| Int16 | putPropertyValueAsSInt16 |
| UInt16 | putPropertyValueAsUInt16 |
| Int32 | putPropertyValueAsSInt32 |
| UInt32 | putPropertyValueAsUInt32 |
| Int64 | putPropertyValueAsInt64 |
| UInt64 | putPropertyValueAsUInt64 |
| Decimal | putPropertyValueAsDecimal |
| Boolean | putPropertyValueAsBoolean |
| UInt32 | putPropertyValueAsDate |
| UInt32 | putPropertyValueAsTime |
| UInt64 | putPropertyValueAsDateTime |
| Byte[ ] | putPropertyValueAsByteArray |

In another exemplary embodiment, XPP requests can go through an 'execution context' and access a 'property' within a 'Property Collection' or nested 'Property Collection'. A 'property value' may be a 'String', 'Integer,' 'Decimal', 'Boolean', 'Date', 'Time', 'DateTime', a 'Byte Array' a 'property collection reference', or an array of 'property collection references'. An XPP can use dot notation (.) 308 to form an address to a 'property.' The first name of an XPP can be a property name 304 of a 'property collection' (e.g., 'Patient'), followed by a 'property path'. For example: Patient.Address.Zip.' An XPP is used by the 'Data Access Methods' on the 'execution context. These methods can be used to get (e.g., read data) and put (e.g., write data), to 'Property Collections.'

Additionally, an XPP can allow for the use of modifiers. A 'modifier' 312 can be used to append additional information to an XPP request. An example of a modifier can be: "Request.NDC?Type=string".

The modifier above can inform an XPP manager to return the NDC as a 'string' value. Modifiers are normally used within the 'qualification engine' to transform a 'property value' to a specific data type. Modifiers are rarely used when using the data access methods to get a 'property value.' This technique can be used extensively in 'multi-phase transaction processing' systems.

In another embodiment, if an XPP 'property path' 302 is being used to address a 'property' in a 'nested—property collection', the 'property path' can consist of at least two components:

<property name>.<property name>

A 'dot notation' can be used to separate each component. Each component can include an optional array indexer 306.

For each level of nesting a '. property name>' can be added to the 'property path.' For example, the 'property path' to address the patient's zip code FIG. 2A would be: 'Address.

In another embodiment, a 'Property Collection' can be persisted/converted into various forms of memory representations and/or media (e.g., JSON object, SQL Database, BLOB (e.g., flat file, cache, immutable storage technology, etc.). For example, the process of converting a 'Property Collection' into a JSON object is a straightforward process, as it is a one-to-one conversion:

A 'property name' maps to a JSON 'key.'
A 'property value' maps to a JSON 'value.'
In another embodiment, the process of converting a 'Property Collection' into a row in a 'SQL Table' is a straightforward process, as it is a one-to-one conversion:

A 'property name' maps to a 'column name' in the 'SQL Table.'
A 'property value' maps to a 'column value' in the 'SQL Table.'

In another embodiment, the process of converting a 'Property Collection' into a Binary Large Object (BLOB) can be accomplished using a process called 'serialization.'

Figures 4B, 4C:
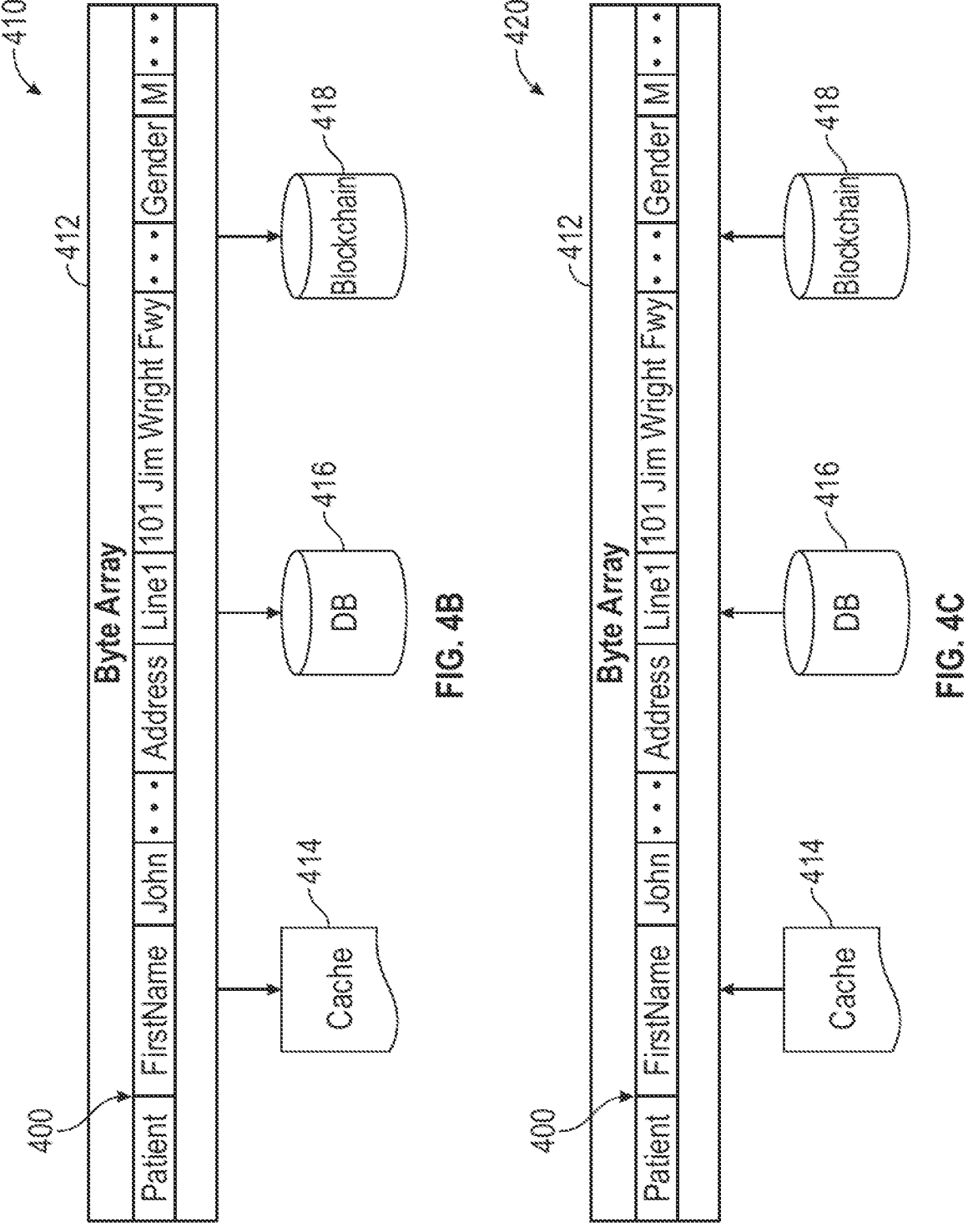

FIGS. 4A-4C illustrate diagrams of a serialized byte array 400, writing byte arrays 410, and reading byte arrays 420, respectively, in accordance with one or more embodiments of the present disclosure. Referring to FIG. 4A, a serialized byte array 400, can include Property Collection properties and associated vales converted into a serial format, such as a JSON, CSV, etc. In one embodiment, serialization can be the process of converting a 'Property Collection' into a 'byte array' such that the contents of the 'Property Collection' can be written to, and read from, a BLOB based storage medium in an efficient manner. For example, a 'Patient' 'Property Collection' can include property fields and values 404, 406, 408. A 'FirstName' property field 404 can include the property name, an associated value (e.g., John) and metadata. An 'Address' property field 406 can include the property name, an associated value (e.g., 101 Jim Wright Fwy) and metadata. If the 'Address' property field is an array, all of the additional array values could follow the first array. A 'Gender' property field 408 can include the property name, an associated value (e.g., M) and metadata. In another embodiment, serialization can support an optional 'Property Name Mapping', which can allow a property name string to be converted to an integer. This process reduces the size of the 'byte array' significantly.

In one embodiment, a 'property collection' can begin with a 'property count' stored as a variable size integer stored in Big-Endian format. A 'property' can consist of a name and value pair. A 'property name' can be stored in an ASCII UTF-8 format. A 'property' value can be a 'String,' 'Decimal,' 'Boolean,' 'DateTime,' 'Date,' 'Time,' 'Integer,' or a "Byte Array." A 'String' value can be stored as a collection of bytes. A Boolean value can be stored in a single byte. The 'DateTime', value can be stored as a variable size integer. The 'Date' and 'Time' values can be stored as a variable size integer. All integer values can be stored in Big-Endian format. A 'Decimal' value can be stored as an ASCII string.

In another embodiment, the data format of a 'property name' can consist of two sections: 'property name type' and 'property name bytes.' For example, a 'property name' definition can be:

| Section | Size | Description |
|---|---|---|
| property name type | 1 byte | A property name can be serialized as a 'String' or a variable length 4 byte 'Integer' (i.e. when the property name has been mapped to and ID). The property name type is stored as a single byte. |
| property name size bytes | variable | If the property name is serialized as a 'String', the property name size bytes can contain a variable size integer in Big-Endian format. If the property name is serialized as a variable length integer, the property name size bytes can contain the integer value in Big-Endian format. |
| property name data bytes | variable | If the property name is serialized as a 'String', the property name bytes can contain that string in UTF-8 format. The property name may contain upper and lower case letters, numbers and the following special characters (@#$%^&*_-). |

In another embodiment, the data format of a 'property value' can consist of the following sections: 'property value type,' property value data count,' and 'property value data bytes.' For example, a 'property value' definition can be:

| Section | Size | Description |
|---|---|---|
| property value type | 1 byte | The property value type can be a byte value, in one embodiment, the high order nibble can indicate the type and the lower nibble can define the number of bytes of a variable length integer that can define the number of bytes in the 'property value bytes' section. |

-continued

| Section | Size | Description |
|---|---|---|
| property value data count | variable (1-8 bytes) | A variable length integer value, stored in Big-Endian format, can represent the value for the type or the number of bytes in the 'property value data bytes' section. |
| property value data bytes | variable | If the 'property value type' contains data bytes this section can be present. |

In another embodiment, Serialization Data Types can include:

| Type Code | Value | Size Bytes | Data Bytes |
|---|---|---|---|
| SH_BOOLEAN_FALSE | 0 | | |
| SH_BOOLEAN_TRUE | 1 | | |
| SH_STRING_1 | 10 | 1 | String stored in UTF-8 format. |
| SH_STRING_2 | 11 | 2 | String stored in UTF-8 format. |
| SH_STRING_3 | 12 | 3 | String stored in UTF-8 format. |
| SH_STRING_4 | 13 | 4 | String stored in UTF-8 format. |
| SH_STRING_5 | 14 | 5 | String stored in UTF-8 format. |
| SH_STRING_6 | 15 | 6 | String stored in UTF-8 format. |
| SH_STRING_7 | 16 | 7 | String stored in UTF-8 format. |
| SH_STRING_8 | 17 | 8 | String stored in UTF-8 format. |
| SH_INT_08 | 20 | 1 | |
| SH_UINT_08 | 21 | 1 | |
| SH_INT_16_1 | 30 | 1 | |
| SH_INT_16_2 | 31 | 2 | |
| SH_UINT_16_1 | 35 | 1 | |
| SH_UINT_16_2 | 36 | 2 | |
| SH_INT_32_1 | 40 | 1 | |
| SH_INT_32_2 | 41 | 2 | |
| SH_INT_32_3 | 42 | 3 | |
| SH_INT_32_4 | 43 | 4 | |
| SH_UINT_32_1 | 45 | 1 | |
| SH_UINT_32_2 | 46 | 2 | |
| SH_UINT_32_3 | 47 | 3 | |
| SH_UINT_32_4 | 48 | 4 | |
| SH_INT_64_1 | 50 | 1 | |
| SH_INT_64_2 | 51 | 2 | |
| SH_INT_64_3 | 52 | 3 | |
| SH_INT_64_4 | 53 | 4 | |
| SH_INT_64_5 | 54 | 5 | |
| SH_INT_64_6 | 55 | 6 | |
| SH_INT_64_7 | 56 | 7 | |
| SH_INT_64_8 | 57 | 8 | |
| SH_UINT_64_1 | 60 | 1 | |
| SH_UINT_64_2 | 61 | 2 | |
| SH_UINT_64_3 | 62 | 3 | |
| SH_UINT_64_4 | 63 | 4 | |
| SH_UINT_64_5 | 64 | 5 | |
| SH_UINT_64_6 | 65 | 6 | |
| SH_UINT_64_7 | 66 | 7 | |
| SH_UINT_64_8 | 67 | 8 | |
| SH_DECIMAL_1 | 70 | 1 | A String that represents a Decimal value stored in UTF-8 format. |
| SH_DECIMAL_2 | 71 | 2 | A String that represents a Decimal value stored in UTF-8 format. |
| SH_DATE | 80 | 4 | Example: 20191231 |
| SH_TIME | 81 | 3 | Example: 235959 |
| SH_DATETIME | 82 | 6 | Example: 20191231235959 |
| SH_BYTES_1 | 90 | 1 | Raw bytes |
| SH_BYTES_2 | 91 | 2 | |
| SH_BYTES_3 | 92 | 3 | |
| SH_BYTES_4 | 93 | 4 | |
| SH_BYTES_5 | 94 | 5 | |

-continued

| Type Code | Value | Size Bytes | Data Bytes |
|---|---|---|---|
| SH_BYTES_6 | 95 | 6 | |
| SH_BYTES_7 | 96 | 7 | |
| SH_BYTES_8 | 97 | 8 | |
| SH_PROPERTY_COLLECTION | 100 | | An embedded property collection follows, which consists of an Int32 count (i.e. representing the number of properties to follow) and then the property definitions. |
| SH_PROPERTY_COLLECTION_ARRAY | 101 | | A count of the number of property collections follow and then the embedded property collections. |

Data types that are stored as variable size integers can be stored in Big-Endian format.

In another embodiment, the following, can be an example of a property collection that contains 2 properties and serialized into a 'Byte Array' of 27 Bytes:

| byte offset | byte values | Description |
|---|---|---|
| 0 | 45 | SH_UINT_32_1, 1 Byte integer follows |
| 1 | 2 | A 1 Byte integer, which contains a value of 2 (e.g., 2 properties) |
| 2 | 10 | SH_STRING_1, 1 Byte integer follows |
| 3 | 3 | A 1 Byte integer, which contains a value of 3 (e.g., 3 bytes in name) |
| 4 | "mid" | The character bytes 'm,' 'i,' 'd.' |
| 7 | 10 | SH_STRING_1, 1 Byte integer follows |
| 8 | 6 | A 1 Byte integer, which contains a value of 6. (e.g., 6 bytes) |
| 9 | "123456" | The ASCII characters '1,' '2,' '3,' '4,' '5,' '6.' |
| 15 | 10 | SH_STRING_1, 1 Byte integer follows |
| 16 | 4 | A 1 Byte integer, which contains a value of 4 (4 bytes in property name) |
| 17 | "data" | The character bytes 'd,' 'a,' 't,' 'a.' |
| 21 | 90 | SH_BYTES_1, 1 Byte integer follows |
| 22 | 4 | A 1 Byte variable length integer, which contains a value of 4 (e.g., 4 bytes of data follow) |
| 23 | 0x00, 0x11, 0x22, 0x33 | The data bytes |

Figure 5:
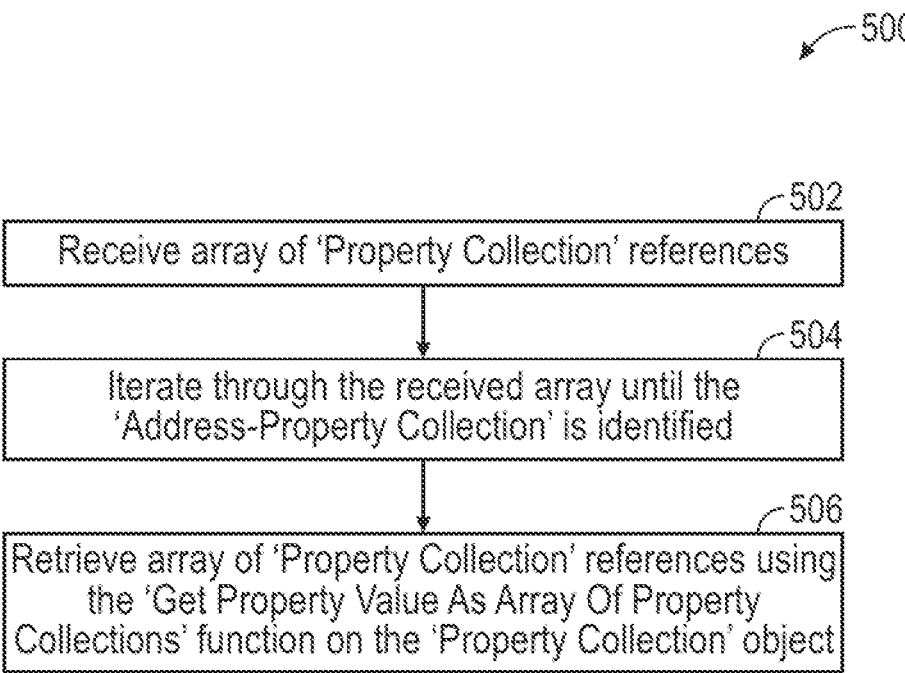
FIG. 5 illustrates a flowchart exemplifying Property Collection array access process flow control logic, in accordance with one or more exemplary embodiments of the present disclosure.

FIG. 5 illustrates a flowchart exemplifying Property Collection (PC) array access process flow control logic 500, in accordance with one or more exemplary embodiments of the present disclosure. The PC array access control logic 500 can be implemented as an algorithm on a server 102, a machine learning module, a client 150, a memory 130, a combination of one or more of the aforementioned components, or other suitable system. The PC array access control logic 500 can be achieved with software, hardware, an application programming interface (API), a network connection, a network transfer protocol, HTML, DHTML, JavaScript, Dojo, Ruby, Rails, other suitable applications, or a suitable combination thereof.

The PC array access control logic 500 can leverage the ability of a computer platform to spawn multiple processes and threads by processing data simultaneously. The speed and efficiency of the PC array access control logic 500 can be greatly improved by instantiating more than one process to implement PC array access. However, one skilled in the art of programming will appreciate that use of a single processing thread may also be utilized and is within the scope of the present disclosure.

Access to a 'Property Collection', within an array, can be accomplished using the following options:

Using 'array' syntax within a 'property path' with a numeric value that represents the 'index' of the 'Property Collection'. For example, a 'property path' of "Addresses [1].Zip" can access the second 'Address—Property Collection' in the 'Addresses' array.

Using 'array' syntax within a 'property path' with a 'starting index' and 'qualification name' that represents the 'qualification logic' associated with the desired 'Property Collection.' This syntax can return the 'first' 'Collection', starting at the 'index' specified, that satisfies the 'qualification' logic. For example: "Addresses[0:ActiveAddress] .Zip"—can be used to retrieve the 'Zip' of the first 'Address—Property Collection', where the value of the 'Address.Active' property is 'true.' This technique can only be used when addressing a 'property collection' through an 'execution context.'

If the 'Property Collection' is being accessed from code, the code can retrieve the array of 'Property Collection' references, and then iterate through that array until it finds the 'Address—Property Collection' of interest. The array of 'Property Collection' references can be retrieved using the 'getPropertyValueAsArrayOfPropertyCollections' method on the 'Property Collection' object.

The PC array access control logic 500 of the present embodiment begins at step 502, where the control logic 500 can receive an array of 'Property Collection' references. The control logic 500 then proceeds to step 504.

At step 504, the control logic 500 can iterate through the received array until the 'Address—Property Collection' is identified. The control logic then proceeds to step 506.

At step 506, the control logic 500 can retrieve an array of 'Property Collection' references using the 'getPropertyValueAsArrayOfPropertyCollections' function on the 'Property Collection' object. The control logic 500 then terminates or awaits a new array of 'Property Collection' references and can repeat the aforementioned steps.

Figure 6:
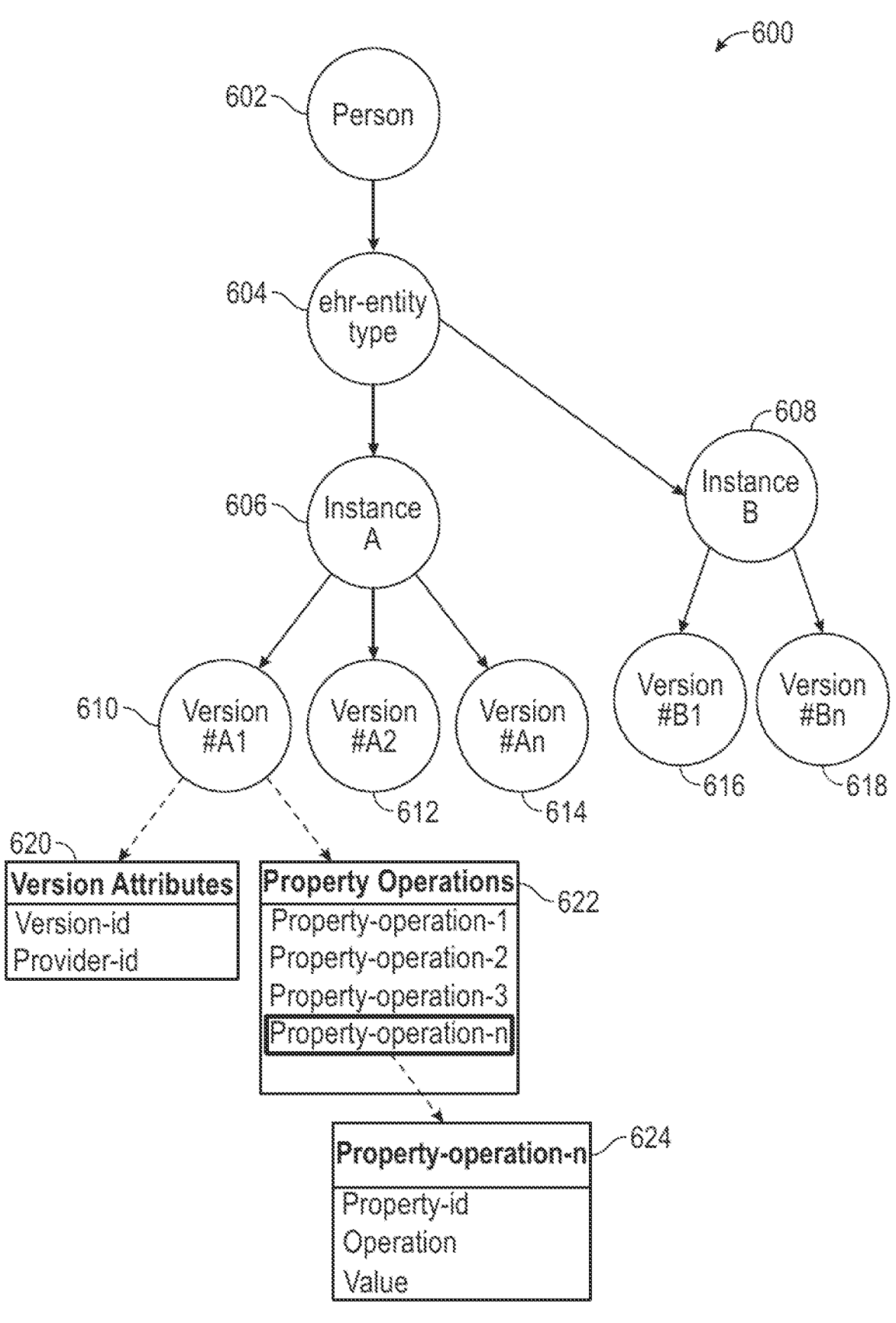
FIG. 6 illustrates a schematic view of a node hierarchy of a Global Person Record, in accordance with one or more exemplary embodiments of the present disclosure.

FIG. 6 illustrates a schematic view of a node hierarchy of a Global Person Record (GPR) 600, in accordance with one or more exemplary embodiments of the present disclosure. In one embodiment, the GPR 600 can be a database of records for a plurality of persons. In another embodiment, the GPR 600 can be stored in memory, on a blockchain, or other distributed ledger. In another embodiment, the GPR can be stored in a property collection management and architecture system (e.g., a cloud-based service, which can exist as multiple instances throughout the world—the instances can be kept in-sync with each other through an nChain-API, a Bitcoin-SV Blockchain, EHR-archival-node, or other suitable system).

The property collection management and architecture system 100 can implement a GPR node hierarchy can establish a framework for organizing data related to a particular person 602. In another embodiment, a person 202 can have a record in the GPR database 600 that can. be identifiable via a unique identifier for the person (person-id). For example, the unique identifier can be an alpha-numeric text string, a name, or other suitable unique identifier. In another embodiment, the person 202 can be a wrapper at the top of the hierarchy and can encompass the attributes, fields, and values related thereto. In another embodiment, the hierarchy can contain an unlimited number of grouping nodes and nodes. In another embodiment, the grouping nodes and nodes can represent different data categories. The grouping nodes and nodes can represent a collection of an entity-type 604 with one or more instance-nodes 606, 608 and one or more associated version-nodes 610, 612, 614 associated with a first instance A 606 and one or more associated version-nodes 616, 618 associated with a second instance B 608. In another embodiment, the entity-type 604 can be a specific type of data within the GPR 600, such as Name, Address, etc. The hierarchy can be expanded to include a plurality of instances having a plurality of versions. In another embodiment, the entity-type 604, instance 606, and versions 610, 612, 614 can be arranged in a hierarchy.

In one embodiment, when an instance of an entity-type 604 is added to a GPR 600, an instance-node 606 can be created to represent the instance. In another embodiment, the ID of the instance-node 606 can be a Universally Unique IDentifier (UUID). In another embodiment, the UUID can be assigned by the client device. By using a UUID, the PUT operation can operate in a distributed environment as the ID of the instance node does not need to be dispensed by a central authority. In another exemplary embodiment, the UUID can be defined as a 128-bit integer (e.g., 0507B3EB-D817-4F27-BBC1-C29B94A155B2). In another embodiment, the UUID can be supplied by a data-provider. In another embodiment, the data-provider can be a client capable of performing PUT operations to create, update, and/or delete data within the GPR 600. Based on the entity-type 604, the instance-node 606 can be created under the specific entity-type node 604 (e.g., Name, Address, Contact Point, etc.). A version-node 610 can also be created and referenced by the instance-node 606. The ID of the version node can be supplied by the data-provider. In another embodiment, the ID of the version node can be a UTC timestamp. The Timestamp can facilitate the ordering of the version nodes 610, 612, 614.

In one embodiment, the version-node 610 can contain a collection of property operations 622 (e.g., operations that affect a property-collection). In another embodiment, the property operations 622, when executed, can create property-id/property-value pairs that can represent the current data values for the entity instance 606 at a specific point in time. In another embodiment, the version-node 610 can also contain a provider-id that can reference the data-provider that supplied the property operations 622. In another embodiment, when properties for an instance are added, updated, or deleted, a new version-node 612 can be created and referenced by the instance-node 606. The new version-node can contain property operations which add new properties, modify existing properties, or delete existing properties defined by property-operations within the previous version-nodes. In another embodiment, the current data values for an instance can be determined by processing the property-operations for each version-node in sequential order by version ID. The resulting ephemeral property-collection can represent the current data items for the instance. In another exemplary embodiment, the property-collection may only exist in cache, can be created on demand, and may never be written to a database or the blockchain. The concept of an instance that supports multiple versions and property-operations within those versions is the mechanism that facilitates the process of tracking data-provider contributions.

In one exemplary embodiment, the system can implement the property-operation values identified in the following table:

| property-operation | Description |
| --- | --- |
| ADD | An ADD operation adds a new property-id and property-value to the property collection of the instance. |
| UPDATE | An UPDATE operation updates a property-value (e.g., which was previously added by an ADD operation within a previous version) within the property collection of the instance. |
| DELETE | A DELETE operation deletes an existing property (e.g., which was previously added by an ADD operation or updated by an UPDATE operation within a previous version) within the property collection of the instance. |

Property Operation Examples

Assuming the following properties:

| property-id | property-name |
| --- | --- |
| 0 | First Name |
| 1 | Middle Name |
| 2 | Last Name |
| 3 | Gender |
| 4 | Date of Birth |
| 5 | Title |

Version-0:

| provider-id = 0 | | |
| --- | --- | --- |
| property-id | property-value | property-operation |
| 0 | John | ADD |
| 2 | Dow | ADD |
| 3 | Male | ADD |
| 4 | 19561101 | ADD |
| 5 | Mr. | ADD |

Current property-id/property-value collection of the instance:

| property-id | property-value |
| --- | --- |
| 0 | John |
| 2 | Dow |
| 3 | Male |
| 4 | 19561101 |
| 5 | Mr. |

Version-1:

| provider-id = 1 | | |
|---|---|---|
| property-id | property-value | property-operation |
| 1 | Frank | ADD |
| 2 | Doe | UPDATE |

Current property-id/property-value collection of the instance:

| property-id | property-value |
|---|---|
| 0 | John |
| 1 | Frank |
| 2 | Doe |
| 3 | Male |
| 4 | 19561101 |
| 5 | Mr. |

Version-2:

| provider-id = 0 | | |
|---|---|---|
| property-id | property-value | property-operation |
| 5 | | DELETE |

Current property id/value collection of the instance:

| property-id | property-value |
|---|---|
| 0 | John |
| 1 | Frank |
| 2 | Doe |
| 3 | Male |
| 4 | 19561101 |

In operation, in one embodiment, the property collection management and architecture system 100 having servers, processors, machine readable instructions, and memory, can select a person from directory/table having a list of names, or receive a name along with a data request received from a client over a network. In another embodiment, in time order, the system can generate a property collection for a person, within the person's hierarchy, and a timestamp of the property collection generation. The system can open the first property collection created by, for example, Pharmacy 1. Additional property collections can be nodes that exist as different instances (e.g., Instance A 606, Instance B 608, to Instance n) or different versions (e.g., Version #A1 610, Version #A2 612, to Version #An 614) for a particular person with the different nodes being data received from hospitals, insurance companies, laboratories, etc. In one embodiment, the Version nodes can include one or more version attributes 620 or property operations 622. The property operations 622 can further have property-operation-attributes 624 (e.g., property-id, operation, value, etc.). All the property collections for a person may have the same or different data. Many times, the data may have only a few common entries, such as name and address, among others.

The property collection management and architecture system 100 can generate an empty property collection and add a first name, using the aforementioned property-operations, from a request for data that was received from a client

150. In one embodiment, the property collection management and architecture system 100 can identify that a person's last name is missing from the property collection created from the request, and can add, via one or more processors, a last name from one of the other property collections for a particular person. In another embodiment, the property collection can have a typo in the first name and the system can identify differences in the first name field. For example, one or more processors can execute a difference command, or correlate the ASCII values between the two fields, or hash the fields (or a portion thereof) and determine the differences, or other suitable operation to determine differences. In another exemplary embodiment, the property collection management and architecture system 100 can correlate a field of a property collection across multiple timestamps to identify the correct first name and can overwrite the first name field in the property collection with a typo to correct the typo. For example, the property collection management and architecture system 100 can conduct a statistical analysis (e.g., average, mean, median, etc.) of the values of the field over multiple time entries to identify the correct field value. In another exemplary embodiment, the property collection management and architecture system 100 can automatically attempt to retrieve data relevant to a particular request. Advantageously, the end result of these operations (to the extent the data is available) is that validated data is returned to a data-consumer, such that any missing information is provided and any erroneous information is corrected.

In one exemplary embodiment, the property collection management and architecture system 100 can build a history through these commands and can create a property collection for any moment in time, with a timestamp added as metadata to the collection. The provider that provides the missing data can be annotated with the property operation such that an audit trail can be created for verification or monetization purposes. By using timestamps for each property collection, information for a person for a particular date can be identified and retrieved. If data is errantly changed, the data just prior to the errant data change can be repopulated. In another embodiment, the property collection management and architecture system 100 can effectively track, on a field-by-field basis, who contributed data for a particular property collection. So, for any moment in time, the property collection management and architecture system 100 can identify the contribution and identify who provided it.

Although one or more embodiments may reference a patient, the present disclosure applies to any type of entity, whether a person, patient, customer, company, or other suitable entity capable of having data stored in a record associated with that entity. Similarly, although certain embodiments may reference electronic health records, the systems, methods, and concepts disclosed herein are equally applicable to any storage system or record type.

Persons skilled in the art will readily understand that advantages and objectives described above would not be possible without the particular combination of computer hardware and other structural components and mechanisms assembled in this inventive system and described herein. Additionally, the algorithms, methods, and processes disclosed herein improve and transform any general-purpose computer or processor disclosed in this specification and drawings into a special purpose computer programmed to perform the disclosed algorithms, methods, and processes to achieve the aforementioned functionality, advantages, and objectives. It will be further understood that a variety of programming tools, known to persons skilled in the art, are available for generating and implementing the features and operations described in the foregoing. Moreover, the particular choice of programming tool(s) may be governed by the specific objectives and constraints placed on the implementation selected for realizing the concepts set forth herein and in the appended claims.

The description in this patent document should not be read as implying that any particular element, step, or function can be an essential or critical element that must be included in the claim scope. Also, none of the claims can be intended to invoke 35 U.S.C. § 112(f) with respect to any of the appended claims or claim elements unless the exact words "means for" or "step for" are explicitly used in the particular claim, followed by a participle phrase identifying a function. Use of terms such as (but not limited to) "mechanism," "module," "device," "unit," "component," "element," "member," "apparatus," "machine," "system," "processor," "processing device," or "controller" within a claim can be understood and intended to refer to structures known to those skilled in the relevant art, as further modified or enhanced by the features of the claims themselves, and can be not intended to invoke 35 U.S.C. § 112(f). Even under the broadest reasonable interpretation, in light of this paragraph of this specification, the claims are not intended to invoke 35 U.S.C. § 112(f) absent the specific language described above.

The disclosure may be embodied in other specific forms without departing from the spirit or essential characteristics thereof. For example, each of the new structures described herein, may be modified to suit particular local variations or requirements while retaining their basic configurations or structural relationships with each other or while performing the same or similar functions described herein. The present embodiments are therefore to be considered in all respects as illustrative and not restrictive. Accordingly, the scope of the inventions can be established by the appended claims rather than by the foregoing description. All changes which come within the meaning and range of equivalency of the claims are therefore intended to be embraced therein. Further, the individual elements of the claims are not well-understood, routine, or conventional. Instead, the claims are directed to the unconventional inventive concept described in the specification.

What is claimed is:

1. A system for property collection management and architecture, comprising:

a global patient record database storing a plurality of property collections; and a computer processor operably coupled to the global patient record database and configured to execute machine-readable instructions, wherein the configuration of the computer processor to execute the machine-readable instructions includes configuration to spawn a first computer process configured to execute a first set of instructions of the machine-readable instructions to perform a first set of program steps for facilitating electronic health record data qualification and to spawn a second computer process configured to execute a second set of instructions of the machine-readable instructions to perform a second set of program steps for facilitating electronic health record data qualification, wherein the first computer process and the second computer process are spawned concurrently, wherein the first set of program steps and the second set of program steps include one or more of program steps comprising:

generating an empty property collection for a person, the property collection having an execution context property path (XPP), wherein the XPP comprises an American Standard Code for Information (ASCII) string including a property collection name and a property path, wherein the property path includes array syntax specifying a starting index and a qualification name corresponding to qualification logic, wherein the array syntax returns a first property collection, starting at the starting index, that satisfies the qualification logic, wherein the array syntax is usable exclusively through an execution context;

adding a plurality of fields from a request for data that was received from a client to the property collection;

identifying empty fields in the property collection;

searching other property collections for the person and adding missing data to the property collection for the person;

identifying differences in a first field of the other property collections by correlating ASCII values between the first field of the other property collections; and conducting a statistical analysis of the ASCII values of the first field of the other property collections over multiple time entries to identify a correct first field value.

2. The system of claim 1, wherein the correlation can include a field of a property collection across multiple timestamps to identify the correct first data field and can overwrite the first data field in the property collection.

3. The system of claim 1, wherein the statistical analysis can include an average, mean, or median.

4. The system of claim 1, the program steps further comprising returning validated data to the client, such that any missing information is provided and any erroneous information is corrected.

5. The system of claim 1, the program steps further comprising building a history of commands to create a property collection for different times.

6. The system of claim 1, the program steps further comprising adding a timestamp as metadata to the property collection.

7. The system of claim 1, the program steps further comprising annotating a provider of missing data.

8. The system of claim 1, the program steps further comprising annotating a property operation such that an audit trail can be created.

9. The system of claim 1, the program steps further comprising using timestamps for each property collection, to identify and retrieve information for the person for a particular date.

10. The system of claim 1, the program steps further comprising repopulating data just prior to an errant data change.

11. A method of property collection management and architecture by a computing system, the computing system including one or more processors configured to execute computer program instructions, comprising:

spawning a first computer process configured to execute a first set of computer program instructions of the computer program instructions to perform a first set of steps of the method of property collection management and architecture;

spawning, concurrently with the spawning of the first computer process, a second computer process configured to execute a second set of computer program instructions of the computer program instructions to perform a second set of steps of the method of property collection management and architecture;

generating an empty property collection for a person, the property collection having an execution context property path (XPP), wherein the XPP comprises an American Standard Code for Information (ASCII) string including a property collection name and a property path, wherein the property path includes array syntax specifying a starting index and a qualification name corresponding to qualification logic, wherein the array syntax returns a first property collection, starting at the starting index, that satisfies the qualification logic, wherein the array syntax is usable exclusively through an execution context;

adding a plurality of fields from a request for data that was received from a client to the property collection;

identifying empty fields in the property collection;

searching other property collections for the person and adding missing data to the property collection for the person;

identifying differences in a first field of the other property collections by correlating ASCII values between the first field of the other property collections; and conducting a statistical analysis of the ASCII values of the first field of the other property collections over multiple time entries to identify a correct first field value.

12. The method of claim 11, wherein the correlation can include a field of a property collection across multiple timestamps to identify the correct first data field and can overwrite the first data field in the property collection.

13. The method of claim 11, wherein the statistical analysis can include an average, mean, or median.

14. The method of claim 11, further comprising returning validated data to the client, such that any missing information is provided and any erroneous information is corrected.

15. The method of claim 11, further comprising building a history of commands to create a property collection for different times.

16. The method of claim 11, further comprising adding a timestamp as metadata to the property collection.

17. The method of claim 11, further comprising annotating a provider of missing data.

18. The method of claim 11, further comprising annotating a property operation such that an audit trail can be created.

19. The method of claim 11, further comprising using timestamps for each property collection, to identify and retrieve information for the person for a particular date.

20. The method of claim 11, further comprising repopulating data just prior to an errant data change.

* * * * *